United States Patent [19]

Soowal

[11] Patent Number: Plant 5,727

[45] Date of Patent: Apr. 22, 1986

[54] FICUS PLANT

[76] Inventor: Jerry Soowal, 1900 N. Federal Hwy., Dania, Fla. 33004

[21] Appl. No.: 593,721

[22] Filed: Mar. 26, 1984

[51] Int. Cl.[4] ..... A01H 5/00

[52] U.S. Cl. ..... Plt./88

[58] Field of Search ..... Plt./88, 51

*Primary Examiner*—Robert E. Bagwill

*Attorney, Agent, or Firm*—Frijouf, Rust & Pyle

[57] ABSTRACT

A new and distinct variety of Ficus plant, having leaves more ovate in shape, a straighter trunk, the trunk and main branches of a lighter grey color, and being more resistant to thrip infestation than its parent *Ficus microcarpa.*

3 Drawing Figures

BACKGROUND OF THE INVENTION

The opportunity and need for interior landscaping in commercial settings such as shopping malls has increased dramatically in recent years. Not only are low lying shrubs used, but medium sized plants and even trees are now in demand, particularly in the larger shopping malls. Several varieties of Ficus have been used in these commercial settings with varying degrees of success. The *Ficus benjamina* was one of the early and well-known favorites. The *benjamina* is characterized by relatively wide elliptical leaves having a dark green color and a rippled surface. Although the *benjamina* tends to develop heavy foliage in the nursery, when it is transplanted to a mall environment with reduced light levels, the heavy foliage does not permit sufficient light penetration and significant leaf droppage is a common result. In addition, the *Ficus benjamina* is overly sensitive to handling and shipment and often suffers after mall plantings. It requires approximately 250 foot candles of illumination to maintain its appearance and although some interior commercial settings provide that much illumination, many do not.

The *Ficus microcarpa,* often referred to in the trade as *Ficus nitida,* has increased greatly in popularity both in an absolute sense and relative to the *Ficus benjamina.* The *microcarpa* is similar to the *benjamina* except that the leaves usually are not quite as dark a green, and they have no ripples. The *microcarpa* is generally much hardier than the *benjamina,* and in particular can withstand the stress of the indoor shopping mall environment to such a greater degree that it is probably superior in such applications. However, the canopy of the *microcarpa* tends to spread considerably and the resulting imbalance tends to cause the trunk and main limbs to bend and grow over toward one side. It is difficult to obtain and maintain symmetry of the *Ficus microcarpa* plant. It generally requires staking and bracing in several spots to develop a straight trunk, with considerable pruning to maintain a symmetrical shape. In general, the requirement for more work on the site is an undesirable factor.

A second variety of *F. microcarpa,* often referred to in the trade as *F. retusa,* is of significance primarily because of its increased resistance to thrip infestation. Like the first variety of *F. microcarpa* discussed in the preceding paragraph, this second variety of *F. microcarpa* is hardier than *benjamina,* and therefore better suited to the rigors of commercial use such as the indoor shopping mall environment. Unfortunately, it also tends to spread its canopy and grow into an unsymmetrical shape, like the first variety of *F. microcarpa.*

The new variety, to be known as *Ficus elegante',* was discovered by me as a sport limb originating on a specimen of the second variety of *F. microcarpa* plant in my nursery at Dania, Fla. I was engaged in large scale production of various Ficus varieties at the time, and in particular I was interested in developing improvements upon the cultivar consisting of the second variety of *F. microcarpa.* The original sport limb discovered by me was remarkably different from the other limbs on the parent *nitida F. microcarpa* in that all the leaves on this limb were relatively ovate, whereas the remainder of the parent plant had the typically elliptical leaves of the *F. microcarpa.* The air layering process was used for propagation, and soon there existed several whole plants of the new variety. All of these young plants exhibited the same peculiar leaf shape as previously described on the originally discovered sport limb.

Other distinguishing characteristics of the new variety were noted as the sample plants grew to maturity. In particular, the trunks and main branches were of a light grey color, significantly lighter than that of the parent *Ficus microcarpa.* The secondary branches tended to be darker, just as in the *F. microcarpa.* Whereas the canopy of the *Ficus nitida* and the *microcarpa* tends to spread considerably and the trunk tends to bend to one side as the tree matures, the new variety tends to have less spread in the canopy, a far more symmetrical shape, and a relatively straight trunk. As the new variety approaches maturity, the canvas is relatively thick but well proportioned, not spreading unduly so as to cause balance problems. The branching structure is uniform, which tends to enhance the symmetry of the adult plant.

Reproduction of the new variety through more than three generations has been accomplished by the air layering process. The plants of each generation to date all have the same appearance as the original sport limb mutation found on the *Ficus microcarpa.* The other characteristics described herein are also common to all plants of the new variety reproduced to date.

In my nursery the large scale production of various varieties of Ficus is primarily for use in the commercial environment, particularly in shopping malls. In general, plants are grown to approximately the desired size at relatively high illumination levels and under other conditions which are beneficial to healthy growth. Subsequently, most of my plants are subjected to steadily diminishing illumination levels so as to acclimate them to the conditions anticipated in locations such as shopping malls. When specimens of the new variety were subjected to the same diminishing levels of illumination as were other varieties such as *Ficus benjamina,* and *F. microcarpa,* it was discovered that the new variety would maintain its appearance at sustained levels as low as approximately 150 foot candles of illumination. By contrast, the *Ficus microcarpa* requires approximately 200 foot candles or more, and the *benjamina* generally requires more than 250 foot candles of illumination.

Growing samples of the new variety along side samples of *Ficus benjamina, Ficus microcarpa* in my nursery also demonstrated another significant characteristic of the new variety. As is well known, the foliage of the *Ficus benjamina* suffers considerably from thrip infestation. The first variety of *Ficus microcarpa* also tends to be affected adversely by thrips. The second variety of *F. microcarpa* consistently shows more resistance to thrip infestation than does either the first variety or the *benjamina.* In my nursery, the samples of the new variety proved even more resistant to thrip infestation than the second variety of *Ficus microcarpa.*

DESCRIPTION OF THE PREFERRED EMBODIMENT

Figure 1:
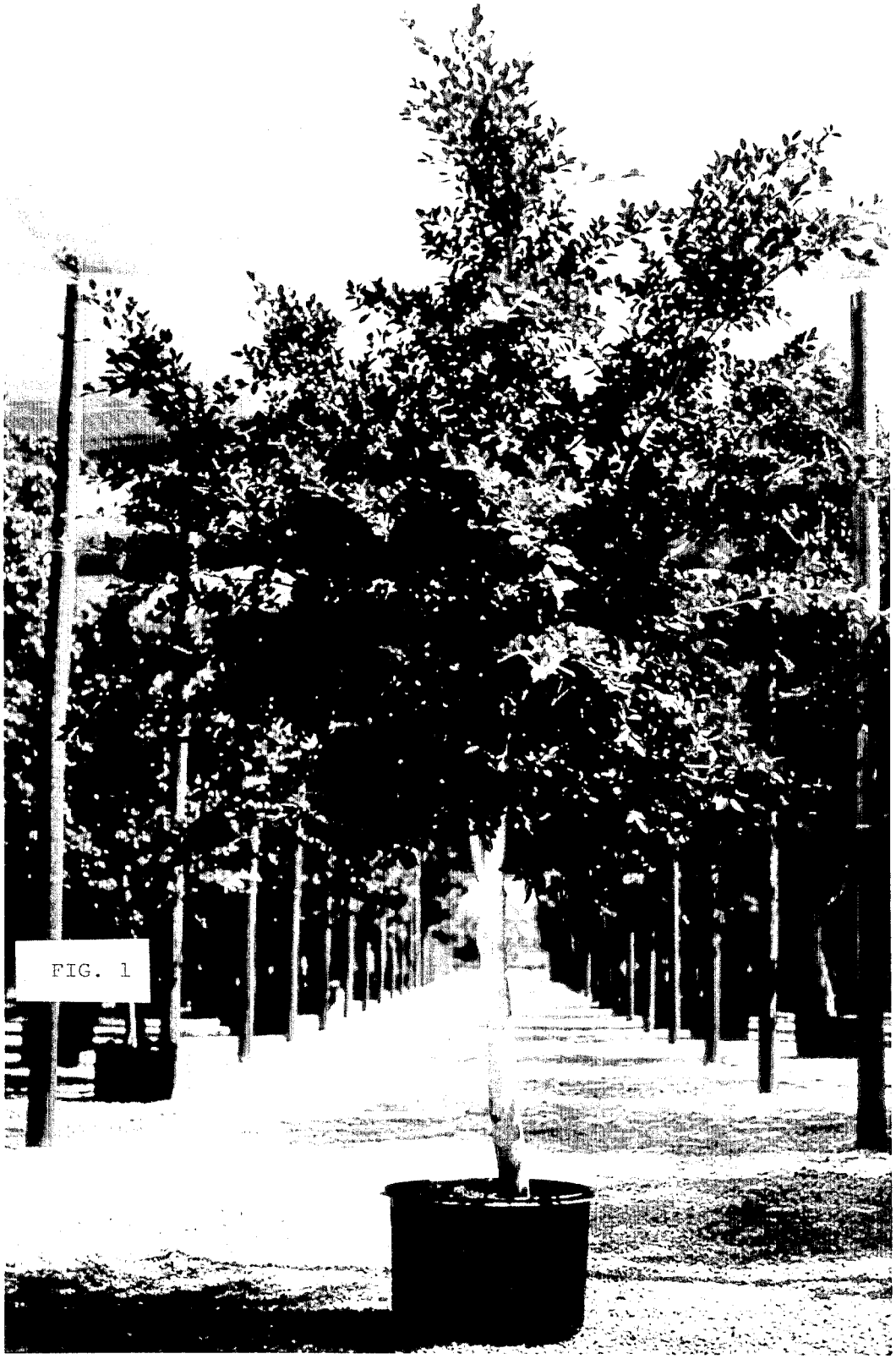
FIG. 1 is a color photograph of a specimen of the new variety showing the symmetry tendency and the light grey color of the trunk and main branches.
Figure 2:
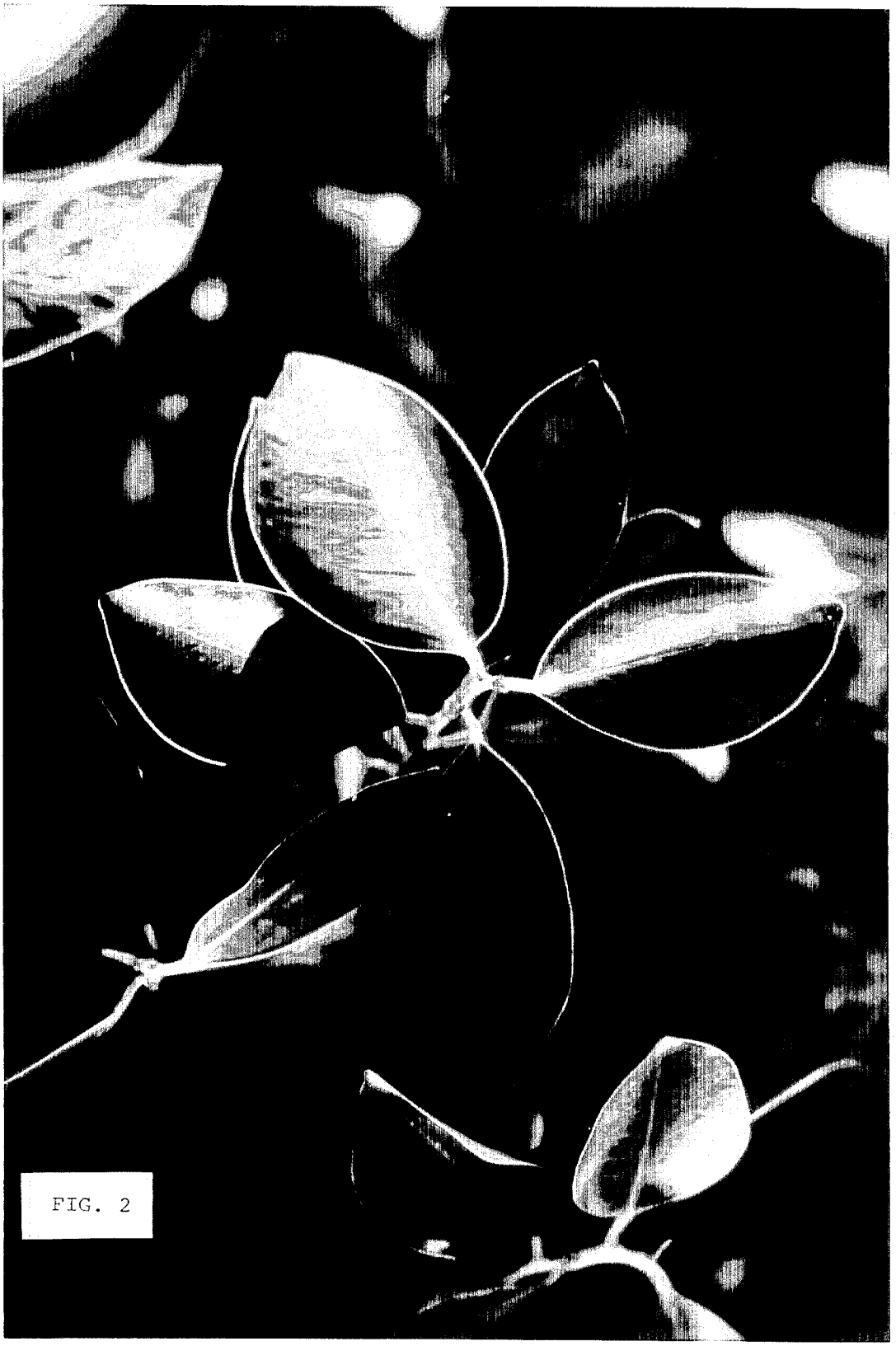
FIG. 2 is a color photograph showing the leafing structure on a branch of the new variety.
Figure 3:
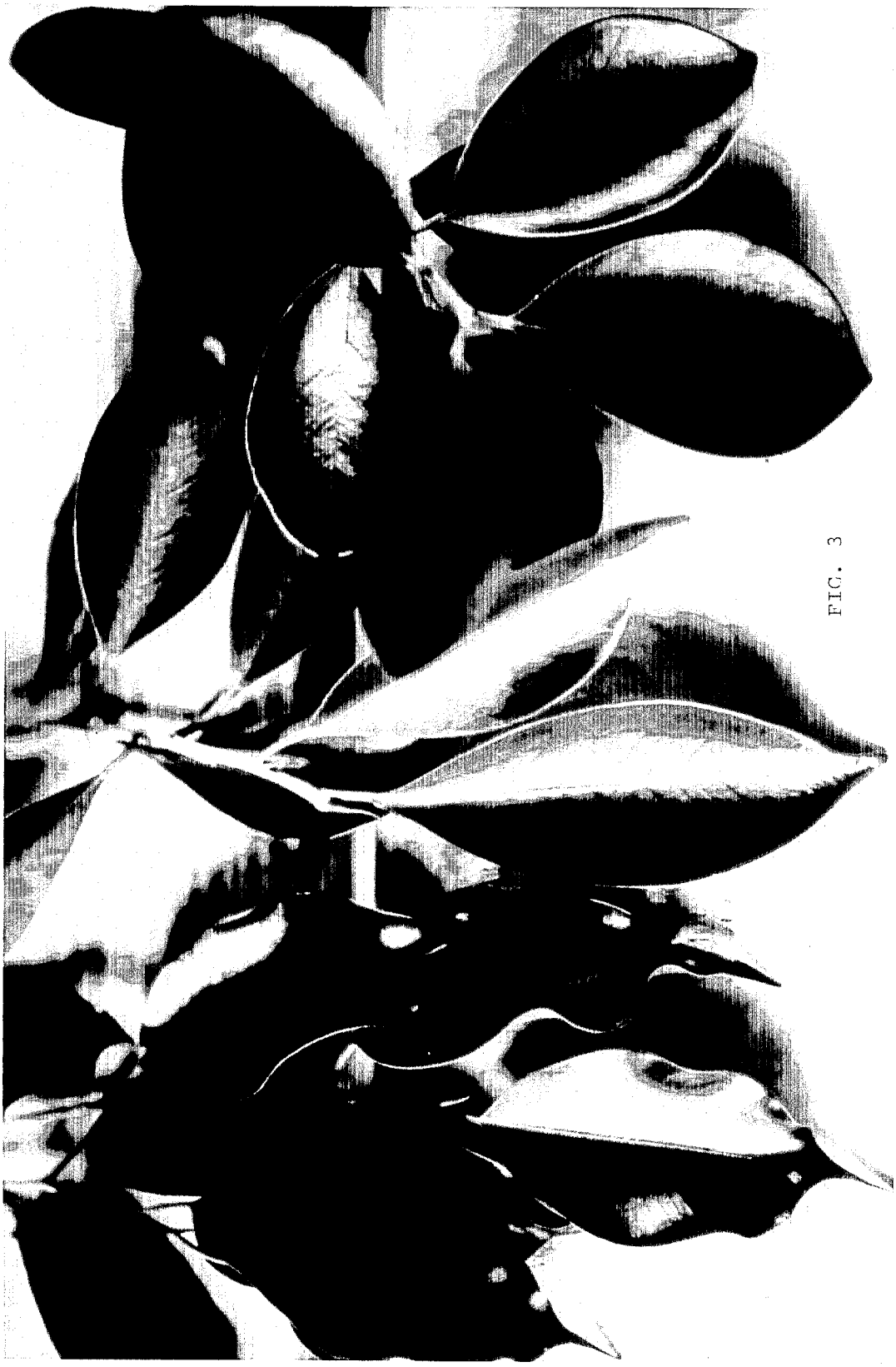
FIG. 3 is a color photograph showing sample leaves of the *Ficus benjamina* at the left of the picture, that of the parent *Ficus microcarpa* in the center of the picture, and that of the new variety of *F. microcarpa* at the right of the picture, all three samples having been picked at approximately the same time just prior to the taking of the photograph.

The mature tree of the new variety is characterized by having a relatively thick canvas contained in a full, symmetrical form. The relative symmetry tends to remain even when the plant is subjected to relatively low light levels for significant periods of time. The general symmetry exhibited by the new variety is due in part to the uniform branching structure which tends to produce an evenly proportioned overall shape while still allowing some open spaces between branches.

The trunk of the new variety is remarkably straight for a Ficus, consistent with the general symmetry of the plant. The trunk is of a light grey color, and the same color is carried into the main branches. The secondary branches tend to be darker just as in many samples of the *Ficus benjamina* and *Ficus microcarpa.*

The leafing structure of the new variety is of the simple type just as in the *Ficus benjamina* and the *microcarpa.* The individual leaves are smooth and concave, and have no ripples on the surface. The margin of the leaf is smooth and continuous. The leaf shape is more ovate than elliptical, although the base is acute, as is the tip. Venation, although not pronounced, is parallel from midrib to margin. Leaf color is similar to most samples of *Ficus microcarpa,* all of these being a relatively dark green but usually not quite as dark a green as that of the *Ficus benjamina.*

The new variety is more resistant to thrip infestation than the *Ficus microcarpa* and remarkably more thrip resistant than the *Ficus benjamina.* Relatively low levels of illumination are tolerated quite well by the new variety. Providing the illumination level is reduced sufficiently slowly to avoid shock, illumination levels as low as approximately 150 foot candles may be sustained by the new variety without having a substantial detrimental effect on the appearance of the plant.

I claim:

1. A new and distinct variety of Ficus plant, substantially as herein shown and described, having leaves the color of its parent *Ficus microcarpa* but with a more ovate shape, and having a straighter trunk, a more symmetrical overall shape, and a trunk and main branches of a lighter grey color than that of *Ficus microcarpa,* and being more resistant to thrip infestation than the parent *Ficus microcarpa.*

* * * * *